United States Patent
Johns et al.

(10) Patent No.: US 9,870,494 B2
(45) Date of Patent: Jan. 16, 2018

(54) MOUNT DEVICE UTILIZING PATTERNED FEATURES FOR RACK ORIENTATION DETECTION

(71) Applicant: Beckman Coulter, Inc., Brea, CA (US)

(72) Inventors: Charles W. Johns, Brownsburg, IN (US); Luciano Brueggemann, Munich (DE); Christian Frenz, Puccheim (DE); Charles Martinez, Yorba Linda, CA (US)

(73) Assignee: Beckman Coulter, Inc., Brea, CA (US)

( * ) Notice: Subject to any disclaimer, the term of this patent is extended or adjusted under 35 U.S.C. 154(b) by 56 days.

(21) Appl. No.: 14/181,421

(22) Filed: Feb. 14, 2014

(65) Prior Publication Data

US 2014/0240096 A1 Aug. 28, 2014

Related U.S. Application Data

(60) Provisional application No. 61/768,350, filed on Feb. 22, 2013, provisional application No. 61/894,769, filed on Oct. 23, 2013.

(51) Int. Cl.
*G06K 7/10* (2006.01)
*G06K 19/07* (2006.01)
(Continued)

(52) U.S. Cl.
CPC ............ *G06K 7/10356* (2013.01); *B01L 9/06* (2013.01); *B01L 9/523* (2013.01); *B01L 99/00* (2013.01);
(Continued)

(58) Field of Classification Search
CPC .......... G06K 19/0723; G06K 7/10356; G06K 19/07773; G01N 35/00732; G01N 2035/0491
(Continued)

(56) References Cited

U.S. PATENT DOCUMENTS 5,993,745 A * 11/1999 Laska ................ B01L 9/06
206/446
7,411,508 B2 * 8/2008 Harazin ........... G01N 35/00732
340/572.7

(Continued)

FOREIGN PATENT DOCUMENTS

| CN | 101002236 A | 7/2007 |
| EP | 1 870 834 A1 | 12/2007 |
| EP | 2 081 128 A1 | 7/2009 |

OTHER PUBLICATIONS

International Search Report and Written Opinion dated May 19, 2014 for PCT Patent Application No. PCT/US2014/016576, 9 pages.

(Continued)

*Primary Examiner* — Thomas Alunkal
(74) *Attorney, Agent, or Firm* — Kilpatrick Townsend & Stockton LLP

(57) ABSTRACT

An embodiment of the invention relates to systems and methods for detecting the orientation of sample carriers using two or more RFID tags. One or two dimensional matrix of equally spaced RFID reader antennas may be positioned beneath or within an area on which racks are placed. The first RFID tag defines the origin of the sample carrier and its geometry. The second and additional RFID tags define the orientations of the sample carrier relative to the matrix of the RFID reader antennas. At least two of the tag antennas on the rack align uniquely with two antennas on the reader matrix. The system energizes each reader antenna and associates the RFID tags aligned with them to the RFID reader antenna's physical position.

8 Claims, 10 Drawing Sheets

(51) Int. Cl.
  *G01N 35/00* (2006.01)
  *B01L 9/06* (2006.01)
  *B01L 9/00* (2006.01)
  *B01L 99/00* (2010.01)
  *G01N 35/04* (2006.01)

(52) U.S. Cl.
  CPC ....... *G01N 35/00732* (2013.01); *G01N 35/04* (2013.01); *G06K 19/0723* (2013.01); *B01L 2200/022* (2013.01); *B01L 2300/022* (2013.01); *G01N 2035/00782* (2013.01); *G01N 2035/00881* (2013.01); *G01N 2035/0418* (2013.01); *G01N 2035/0491* (2013.01)

(58) Field of Classification Search
  USPC ........................ 340/10.1, 572.1, 572.7, 13.26
  See application file for complete search history.

(56) References Cited

U.S. PATENT DOCUMENTS

| | | | |
|---|---|---|---|
| 8,400,306 | B2 | 3/2013 | Trueeb et al. |
| 2005/0280574 | A1 | 12/2005 | Tafas et al. |
| 2008/0024301 | A1* | 1/2008 | Fritchie .................. B01L 3/545 340/572.1 |
| 2010/0123551 | A1* | 5/2010 | Fritchie ............ G01N 35/00732 340/10.1 |
| 2011/0095864 | A1* | 4/2011 | Trueeb ............. G01N 35/00732 340/10.1 |
| 2013/0027185 | A1* | 1/2013 | Lavi ......................... B01L 9/06 340/10.1 |
| 2014/0266620 | A1* | 9/2014 | Iqbal .................... G06F 19/366 340/10.1 |

OTHER PUBLICATIONS

International Search Report and Written Opinion dated May 19, 2014 for PCT Patent Application No. PCT/US2014/016470, 10 pages.

Non-Final Office Action dated Sep. 17, 2015 for U.S. Appl. No. 14/181,517, 8 pages.

Chinese Office Action dated Oct. 17, 2017, for CN Patent Application No. 201480006934.4, with English Translation, 13 pages.

* cited by examiner

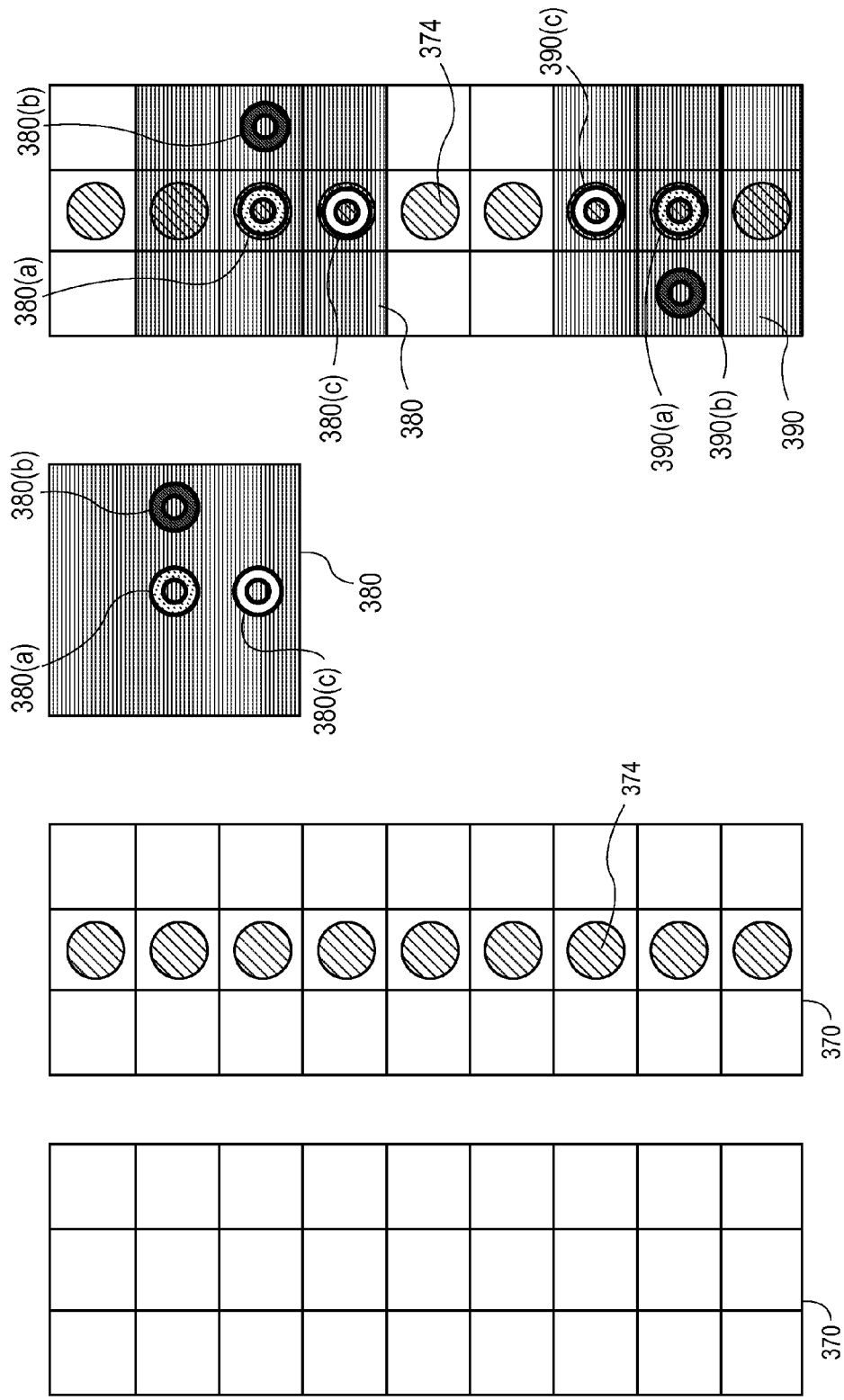

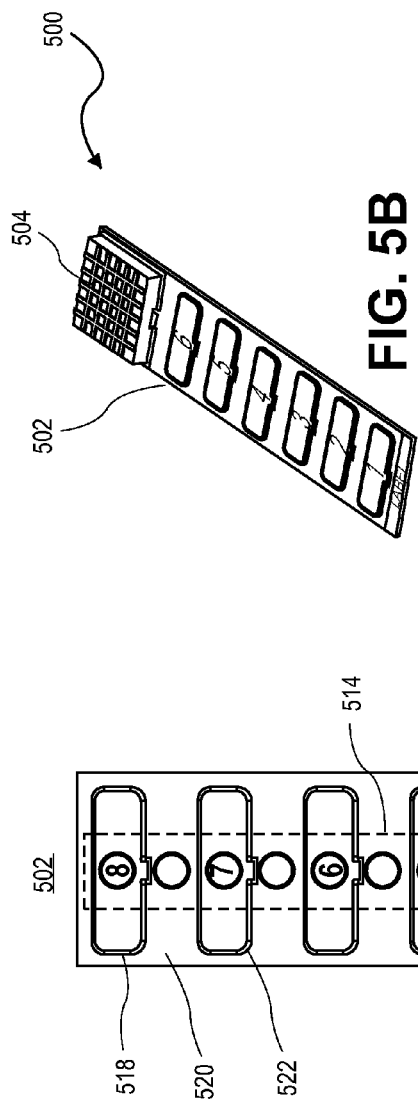
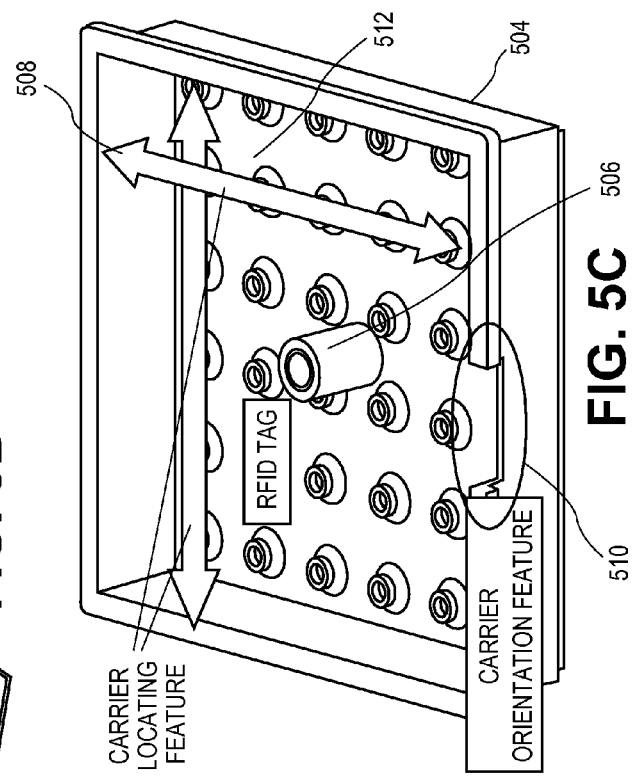
FIG. 5A
FIG. 5B
FIG. 5C

MOUNT DEVICE UTILIZING PATTERNED FEATURES FOR RACK ORIENTATION DETECTION

CROSS-REFERENCES TO RELATED APPLICATIONS

This application claims priority to U.S. Patent Application No. 61/768,350, filed on Feb. 22, 2013 and U.S. Patent Application No. 61/894,769, filed on Oct. 23, 2013, both of which are herein incorporated by reference in their entirety for all purposes.

BACKGROUND

Sample containers may be transported by automated systems in various areas of a laboratory system. Such areas may include input, distribution, centrifuge, decapper, aliquoter, output, sorting, recapping, and secondary tube lift areas. Sample containers may include sample tubes that may contain material for medical analysis, such as blood, serum, gel, plasma, etc. Sample containers may be placed in a rack, tray or sample carrier for storage, processing or for ease of transportation. Racks, trays and sample carriers may also be placed in drawers in specific arrangements to accommodate various workflows or classifications of samples.

Operators of laboratory automation systems can use sample racks to arrange samples in a particular pattern and order to enable the automation equipment to remove samples from these racks based upon their position within the pattern. Likewise, the automation equipment can place samples and sample containers into racks in a particular pattern and order to enable the operator to remove the samples from the racks in a specific pattern and order. If the operator does not orient a rack correctly on the automation equipment, then it is difficult to associate the correct positions within the rack to the sample containers in the rack.

A known solution to overcome the above problem provides loading the racks onto the automation equipment in a unique orientation. A unique feature of the rack can be matched with a mating feature on the automation equipment to accomplish the unique orientation. However, this solution may be frustrating for the operator. It may take multiple attempts for the operator to install the rack onto the automation equipment to obtain the desired orientation.

Another solution, as described by patent application US 2011095864 works for racks having two possible orientations. A square rack having equal length sides could be placed onto the automation equipment in four different orientations. However, with this solution only two out of four possible orientations can be identified. Thus, conventional approaches could be improved.

Embodiments of the invention address these and other problems, individually and collectively.

BRIEF SUMMARY

Embodiments of the invention provide systems and methods that allow an operator to load racks in numerous locations and orientations. An automation system may automatically determine the locations and orientations of the racks (or other sample carrier), as well as any samples of sample containers in the racks.

Embodiments of the invention relate to systems and methods for detecting the orientation of sample carriers or racks using two or more RFID tag antennas. In some embodiments, one or two dimensional matrix of equally spaced RFID reader antennas may be positioned beneath or within an area on which the sample carriers are placed. The first RFID tag defines the origin of the sample carrier and its characteristics (e.g., geometry). The second and additional RFID tags define the orientations of the sample carrier relative to the matrix of the RFID reader antennas. At least two of the RFID tags on the rack can uniquely align with two antennas on the matrix of RFID reader antennas. The system energizes each reader antenna and associates the RFID tags aligned with them to the RFID reader antenna's physical position. The number of detectable locations and orientations is dependent upon the number and spacing of the RFID tag antennas on the rack and the RFID reader antennas within the reader matrix.

One embodiment of the invention is directed to a sample carrier comprising two or more recesses to hold samples or sample containers and two or more RFID tags. At least one out of the two or more RFID tags defines the origin of the sample carrier and the remaining RFID tags define the orientation of the sample carrier.

One embodiment of the invention is directed to a system comprising a sample carrier comprising two or more recesses to hold sample containers and two or more RFID tags, wherein at least one out of the two or more RFID tags defines the origin of the sample carrier and the remaining RFID tags define the orientation of the sample carrier, and a RFID reader antenna matrix, wherein the RFID reader antenna matrix comprises multiple RFID antennas. The RFID reader antennas matrix is positioned beneath or within an area on which the sample carrier is placed. At least two of the RFID tags on the sample carrier align uniquely with at least two antennas on the RFID reader antenna matrix.

Another embodiment of the invention is directed to a method for using the above-described system. The method may include placing a sample carrier with two or more RFID tags on a platform with an antenna reader matrix, which is activated. A set (e.g., one or more) of antenna readers in the antenna reader matrix then reads information in at least one of the RFID tags, and a processor can determine where the sample carrier is located and can also determine the orientation of the sample carrier relative to a reference point. The two or more RFID tags of the sample carrier may be aligned with the antenna reader matrix in such a way that each of the at least two RFID tags is brought into close proximity to an individual RFID reader antenna of the RFID reader antenna matrix.

One embodiment of the invention is directed to a universal mount device comprising a mount body comprising a plurality of patterned features. The plurality of patterned features are capable of positioning sample carriers of different sizes and/or capable of positioning sample carriers at different locations on the mount body. An RFID reader matrix is coupled to the mount body. The RFID reader matrix may be coupled to the mount body in any suitable manner. For example, in embodiments of the invention, the RFID reader matrix may be embedded within the mount body, in recesses in the mount body, or attached to an outer surface (e.g., top or side surfaces) of the mount body. The RFID reader matrix comprises a plurality of RFID reader antennas. The terms RFID reader antenna matrix, reader antenna matrix, RFID reader matrix and reader matrix are used interchangeably in this specification.

Another embodiment of the invention is directed to a system comprising a universal mount device comprising a mount body comprising a plurality of patterned features and an RFID reader antenna matrix coupled to the mount body. The RFID reader antenna matrix comprises a plurality of RFID reader antennas. The system also comprises a sample carrier comprising a carrier body, a carrier locating feature associated with the carrier body, a carrier orientation feature associated with the carrier body, and an RFID tag coupled to the carrier body. The sample carrier is capable of being positioned by interfacing one or more of the patterned features with the carrier locating feature and the carrier orientation feature.

One embodiment of the invention is directed to a method for using the above-described system. The method comprises placing the sample carrier on the universal mount device, such that the one or more patterned features interface with the carrier locating feature and the carrier orientation feature. The method may include placing a sample carrier with one or more RFID tags on a platform with a universal mount device and an RFID reader antenna matrix, which is activated. A set (e.g., one or more) of antenna readers in the RFID reader antenna matrix then reads information in at least one of the RFID tags, and a processor can determine where the sample carrier is located and can also determine the orientation of the sample carrier.

In one embodiment of the invention, a location of a sample carrier can be detected using a physical control device for orientation. For example, a universal mount device can control the location of a rack at one or more positions in a plane. An array or matrix of RFID reader antennas matching the positions of the universal mount device in the plane can be used to read the RFID tag coupled to a rack body. Since the geometric location of each of the universal mount device's positions is known, the location of the correlating reader antenna is also known. When a tag is centered over any of these positions, only one reader antenna of the array can read the RFID tag. The location of the reader antenna that reads the rack's tag allows the location of the reading antenna to be correlated to the location of the rack in the plane. Thus the geometric location of a rack on the universal mount device can be detected.

In another embodiment, use of two or more strategically placed RFID tags on a rack permits the detection of a rack's orientation when coupled with a universal mount device and RFID reader antenna array or matrix. One of the RFID tags may be used to determine the location of the rack. If the RFID reader antenna array is two dimensional, a second RFID tag spaced a distance from the first RFID tag equal to the distance between adjacent reader antennas in the array permits the orientation to be ascertained. If the RFID reader antenna array is one dimensional and a rack is square and the rack may be oriented in up to four possible orientations, the addition of a third antenna permits the detection of the orientation of the rack in any of the four possible orientations.

These and other embodiments of the invention are described in further detail below.

BRIEF DESCRIPTION OF THE DRAWINGS

A further understanding of the nature and advantages of the different embodiments may be realized by reference to the following drawings.

FIG. 3C-1 shows a rack placement area with a grid.

FIG. 3C-2 shows a rack placement area with a grid and a one-dimensional array of RFID antennas.

FIG. 3C-3 shows a square shaped rack (recesses for sample tubes are not shown) 380 with an origin RFID tag, and a first orientation RFID tag, and a second orientation RFID tag.

FIG. 3C-4 shows examples of valid rack placements on the grid.

FIG. 4 illustrates a 60° orientation for a rack using a two-dimensional reader antenna matrix, in one embodiment of the invention.

FIG. 5A illustrates a top plan view of a universal mount device, in one embodiment of the invention.

FIG. 5B illustrates a perspective view of an exemplary rack on a universal mount device, in one embodiment of the invention.

FIG. 5C illustrates an exemplary rack comprising a carrier location feature and a carrier orientation feature, in one embodiment of the invention.

DETAILED DESCRIPTION

Figure 1A:
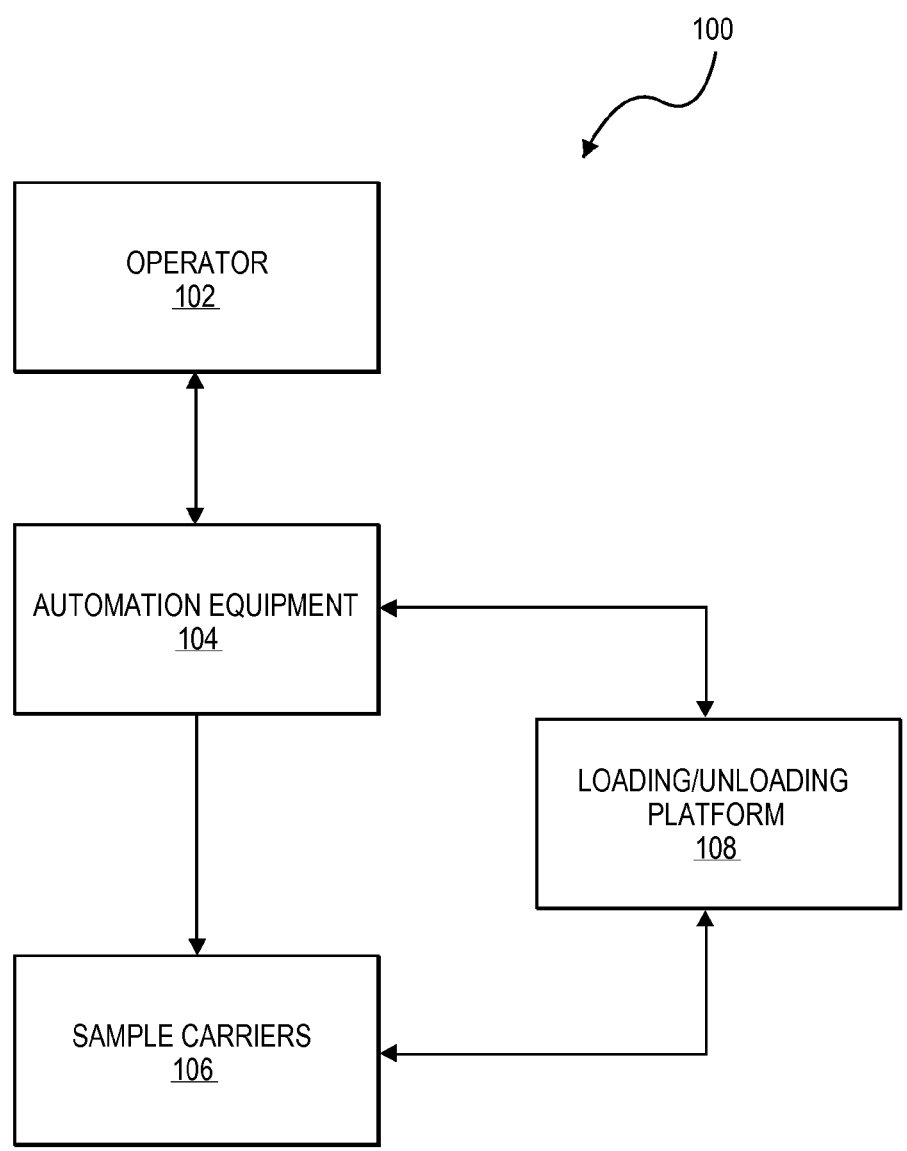
FIG. 1A illustrates a block diagram of a laboratory system.

Laboratory automation systems provide automated sample loading, sorting and unloading/transporting to minimize manual handling. Samples may need to be transported to other instruments or lab sections for storage, further processing or disposal. An operator of a laboratory automation system can associate a specific position within a sample carrier or rack to a specific position within a laboratory automation system. Current solutions allow loading the racks onto the automation equipment in a predefined manner using mechanical structures and orientation features, thus limiting the options for orientation of the rack onto the automation equipment.

In order to manage the traceability of samples by position within a rack, a correlation between each position in the rack and the automation equipment loading the rack needs to be made. Consequently, both the location of a rack in a plane and the orientation of the rack within that plane need to be communicated to the laboratory automation equipment.

There are at least two ways to communicate location and orientation information to the laboratory automation equipment. In the first way, the location and orientation of a sample carrier can be physically controlled so that the automation equipment knows the location of the sample carrier and can correlate that location to specific positions in that sample carrier. In a second way, the location and/or orientation of the sample carrier can be detected relative to a physical location and that physical location can be correlated to positions in the sample carrier.

Embodiments of the invention relate to systems and methods detecting the physical location and/or orientation of a sample carrier. In a first set of embodiments, the location and orientation of the rack can be detected relative to a physical location and can be correlated to a position in a sample carrier. This can be done, for example, by using two or more strategically placed RFID tags on the sample carrier. In a second set of embodiments, the location and/or orientation of a sample carrier can be detected relative to a physical location and can be correlated to a position in a sample carrier. This can be accomplished using, for example, a mount body with a number of patterned features.

Before discussing specific embodiments of the invention, some descriptions of some terms may be useful.

A "body" of a sample carrier or "sample carrier body" may include any suitable structure that can hold samples. In some cases, a body may comprise a number of recesses (e.g., slots, wells, etc.), where the recesses can hold samples or containers which can hold samples. Suitable examples of sample carrier bodies may include rack bodies and microtiter plate bodies. Suitable bodies may be made of any suitable material including glass, plastic, ceramic, etc. They may also comprise an anti-static material to reduce the likelihood that static electricity may be present during use.

An "RFID tag" can include any suitable device that uses radio-frequency electromagnetic fields to transfer data. In some embodiments, a tag can contain electronically stored information. Some tags are powered by and read at short ranges (up to a few meters) via magnetic fields (electromagnetic induction). Others can use a local power source such as a battery, or else have no battery but collect energy from the interrogating EM field, and then act as a passive transponder to emit microwaves or UHF radio waves (i.e., electromagnetic radiation at high frequencies).

A "matrix" may include an array of elements, where the elements in the array are spaced apart from each other. The spacing between the elements in a matrix may be regular or irregular. Suitable matrices may be in the form of a one dimensional array of elements or a two-dimensional array of elements.

A "recess" may include a space of predefined dimensions in a body. A recess can be in the form of a hole or slot, and may be of any suitable size or shape.

FIG. 1A illustrates a high level block diagram of a laboratory system 100. The system may include automation equipment. The laboratory system 100 may include automation equipment 104, and a plurality of sample carriers 106, and a loading and unloading platform 108.

The automation equipment 104 may include any suitable number of apparatuses including at least one of a sorting, capping, decapping, archiving, aliquoting, etc. apparatuses. It may also comprise container handling apparatuses such as robots that can transfer sample containers. The automation equipment 104 may also comprise one or more computers/servers to automate various functions by utilizing one or more robotic systems. The computer apparatus in the automation equipment 104 may also comprise or be coupled to a database of information. The database of information may store information about the types of sample carriers used in the system, the respective sample carrier geometry information, the orientations of the sample carriers on the platform 108, and the locations of the sample carriers on the platform 108.

An operator 102 may use sample carriers 106 to arrange sample containers (i.e., sample tubes) in a particular order and pattern to enable the automation equipment 104 to deposit and/or remove sample containers or samples from the sample carriers 106. The samples or the sample containers may be present in a specific pattern and order in each sample carrier 106. The operator 102 may further load the racks 106 onto a loading/unloading platform 108 coupled to the automation equipment 104. For example, the loading/unloading platform 108 may be part of an input module of the automation equipment 104 where the samples may be loaded for further processing, such as, sorting, capping, decapping, archiving, aliquoting, etc.

Figure 1B:
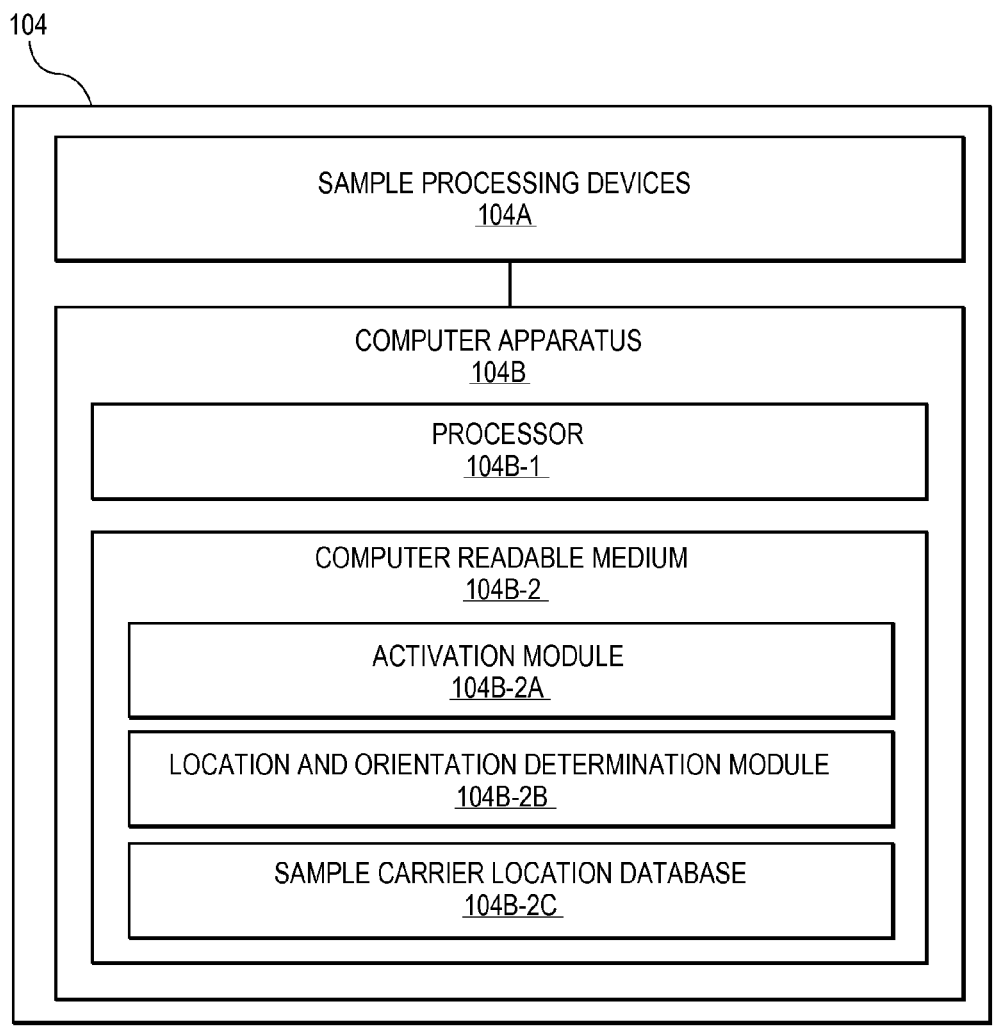
FIG. 1B illustrates a block diagram of components of automation equipment.

FIG. 1B shows a block diagram of some components in automation equipment 104. The automation equipment 104 may include two or more sample processing devices 104A such as sorting, capping, decapping, archiving, aliquoting, etc. devices, as well as devices that can move samples or sample containers (e.g, robots, pipettors, etc.). A computer apparatus 104B may serve as a controller and may control the various sample processing devices.

The computer apparatus 104B may comprise a data processor 104B-1 coupled to a computer readable medium 104B-2. The computer readable medium 104B-2 may comprise any suitable combination of devices that can store data using any suitable data storage mechanism (e.g., electrical, magnetic, optical, etc.). The computer readable medium 104B-2 may comprise a number of software modules including an activation module 104B-2A for activating reader antennas in a reader array. The computer readable medium 104B-2 may also include a type, location and orientation determination module 104B-2B which can be used, in conjunction with the processor 104B-1 to determine the type, location and orientation of the sample carriers after receiving information about which reader antennas detected RFID tags associated with sample carriers. Lastly, the computer readable medium 104B-2 may also include a sample carrier location database 104B-2C which may store the locations of the sample carriers 106 after their locations and orientations have been detected. It is noted that embodiments of the invention are not limited to the specific modules or databases described, but may include more than the specifically described modules and databases.

I. Embodiments Utilizing at Least Two RFID Tags

Some embodiments of the invention utilize a Radio Frequency Identification (RFID) system for detecting the orientation of a rack (or other type of sample carrier) for sample containers in a laboratory automation system. In some embodiments of the invention, the rack possesses two or more RFID tags that define the direction of orientation of the rack. A one or two dimensional matrix of preferably equally spaced RFID reader antennas may be positioned beneath or within an area on which racks may be placed. The RFID antennas may be spaced apart from each other such that neighboring RFID tags to an RFID tag that is activated by a reader antenna are not activated by the reader antenna when the RFID tag is aligned with the reader antenna. A first RFID tag attached to the body of the rack can correspond to the rack origin and a second RFID tag attached to the body of the rack is placed at a pre-determined distance from the first RFID tag. The pre-determined distance matches the distance between at least two antennas in a reader matrix. In some embodiments the distance between any two RFID tags may match the distance between two RFID reader antennas. The matrix and the RFID reader antennas in the matrix may be electrically coupled to a computer apparatus.

The RFID tags may be attached to the body in any suitable manner. For example, the RFID tags may be attached to the body by affixing the two or more RFID tags to a surface of the body, embedding the two or more RFID tags within the body, or allowing the RFID tags to reside in recesses in the body.

As noted above, the first RFID tag defines the origin of the rack and its geometry. The first RFID tag may comprise a memory. In some embodiments, the memory may be used to store the characteristics (e.g., geometry) of the rack. The second and additional RFID tags can be used to define the orientations of the rack relative to the matrix of RFID reader antennas. The second and additional RFID tags can each have a unique value, defining a particular direction within the rack's frame of reference relative to the rack's origin. At least two of the RFID tags of the rack can uniquely align with at least two antennas in an underlying reader matrix in a loading/unloading platform. Thus, the location of the rack and its orientation relative to the RFID reader antenna matrix may be ascertained using embodiments of the invention. Also, using embodiments of the invention, the operator can load racks in numerous locations and orientations, thus providing benefits over conventional systems.

In some embodiments, the use of two or more strategically placed RFID tags on a rack body permits the detection of a rack's orientation when coupled with a universal base frame and an RFID reader antenna array. As noted above, one of the tags can be used to determine the location of the rack. If the RFID reader antenna array is two dimensional, a second tag spaced at a distance from the first tag equal to the distance between adjacent reader antennas in the reader array permits the orientation of the rack to be ascertained. Also, if the RFID reader antenna array is one dimensional, and a rack is square and thus may be oriented in up to four possible orientations, the addition of a third RFID tag in/on the rack body permits the detection of the orientation of the rack in any of the four possible orientations.

The operation of an RFID system can be briefly described before discussing embodiments of the invention. An RFID tag may be include a small electronic chip and an antenna. Individualized data may be encoded in the electronic chip of the RFID tag. Tags such as these may be incorporated into a sample carrier. RFID tags may be active or passive. An active RFID tag may include a power supply to boost the effective operating range whereas a passive tag may function merely with the transmitted power from the RFID reader antenna.

The platform upon which the sample carrier is placed may have a matrix of RFID reader antennas. An RFID reader antenna can include a radio frequency transmitter and receiver that may be controlled by and electrically coupled to a computer apparatus. The RFID reader antenna emits short range radio frequency (RF) signals. The emitted RF signals provide a means for communicating with the RFID tag and provide the RFID tag with power so that the RFID tag can provide a communication back to the RFID reader antenna. When an RFID tag passes through the field of a scanning RFID reader antenna, it detects an activation signal from the RFID antenna. The activation signal wakes up the RFID tag and the RFID tag transmits the information stored in its electronic chip to the scanning RFID antenna. The RFID antenna does not require the RFID tag to be in line of sight to read its stored data.

Figure 2A:
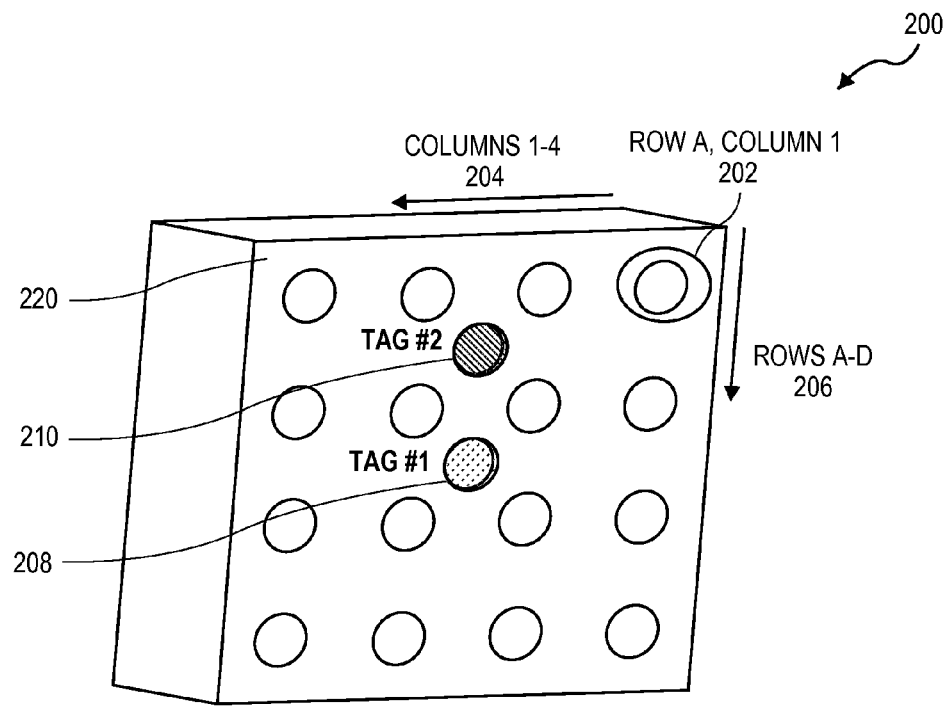
FIG. 2A illustrates an exemplary rack with two RFID tags in one embodiment of the invention.

FIG. 2A illustrates an exemplary rack 200 according to an embodiment of the invention. The rack comprises two RFID tags.

The exemplary rack 200 comprises a body 220 with a square shaped planar cross-section. In this example, the body 220 comprises 16 slots (recesses) for holding sample containers, configured as columns (1-4) 204 and rows (A-D) 206. A slot 202 marks a reference point for row A and column 1. The exemplary rack 200 further comprises a first RFID tag 208 and a second RFID tag 210. Each of the first RFID tag 208 and the second RFID tag 210 may contain electronically stored information that may be read by a RFID reader antenna. In some embodiments, the first and second RFID tags 208 and 210 may each include an integrated circuit for storing and processing information and an antenna for receiving and transmitting signals. The terms "RFID tag antennas", "RFID tags" and "tags" are used interchangeably in this specification.

The body 220 may have any suitable shape including a circular, square or rectangular vertical or horizontal cross section in some embodiments of the invention. It may have any suitable number of slots for holding sample containers, e.g. sample tubes or micro titer plates, in any suitable arrangement. In some embodiments, the slots may be arranged as an array, with equal or unequal numbers of rows and columns.

In one embodiment, the first RFID tag 208 contains information that defines the origin of the rack 200 and its geometry. The second RFID tag 210 can be used to define the orientation of the rack 200. In some embodiments, the distance between the first RFID tag 208 and the second RFID tag 210 is configured so that the orientation of the rack 200 can be determined when the first and second RFID tags 208, 210 are aligned with corresponding reader antennas (not shown) in a matrix of reader antennas in a loading/unloading platform (not shown).

Figure 2B:
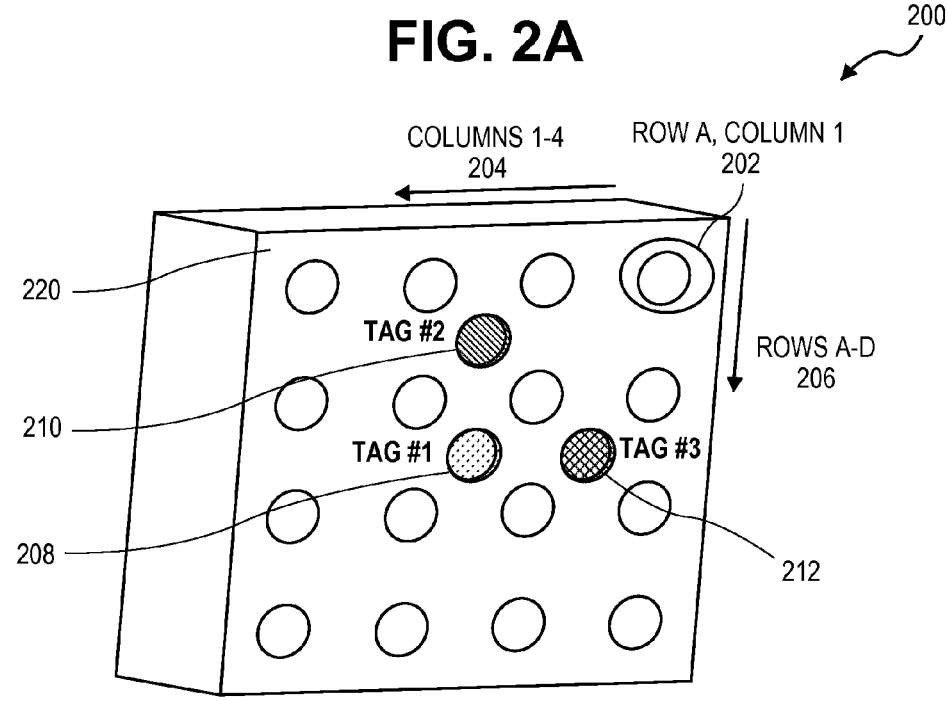
FIG. 2B illustrates an exemplary rack with three RFID tags in one embodiment of the invention.

FIG. 2B illustrates an exemplary rack 201 with three RFID tags according to another embodiment of the invention. In this embodiment, the rack 201 may comprise a third RFID tag 212 in addition to the previously described first and second RFID tags 208 and 210. The third RFID tag 212 may be similar to at least the second RFID tag 210 and may help further define orientation of the rack 201. The locations of the second RFID tag 210 and the third RFID tag 212, with respect to the first RFID tag 208 may be chosen so that at least two of the first, second, and third RFID tags 208, 210 and 212 uniquely align with at least two separate reader antennas in an antenna matrix to determine orientation (and/or location) of the rack 200 on a platform.

Different RFID reader antenna configurations may be used to determine rack orientation as discussed with reference to FIGS. 3A-3B.

Figure 3A:
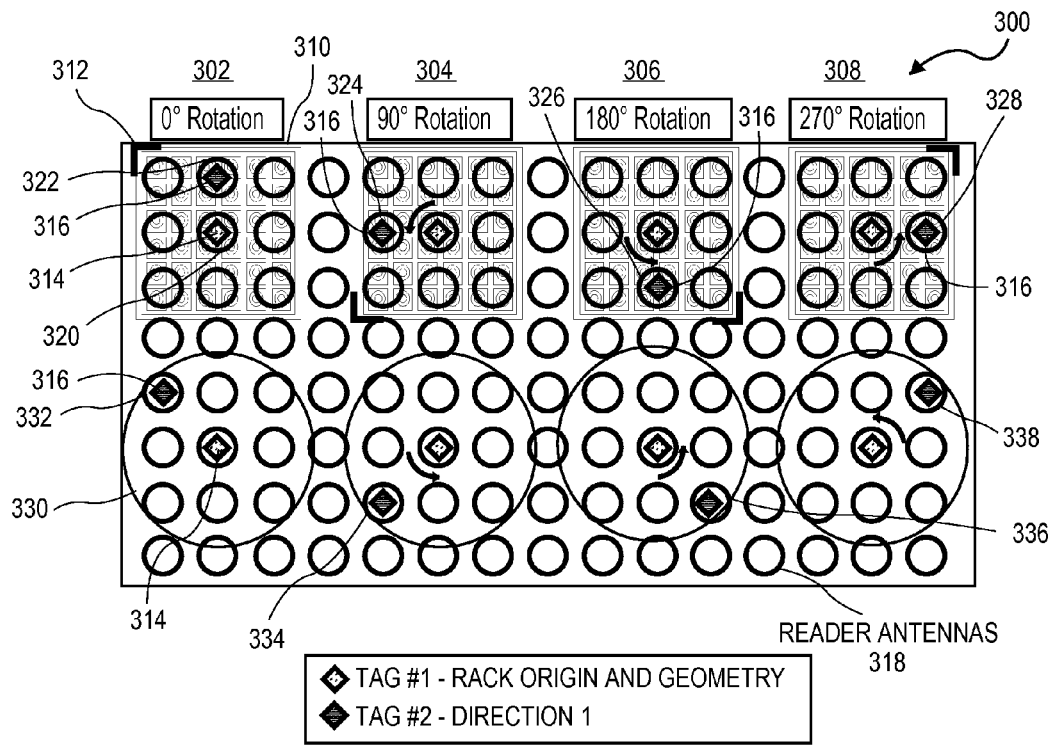
FIG. 3A illustrates different orientations for a rack using a two-dimensional reader antenna matrix, in one embodiment of the invention.

FIG. 3A illustrates how different orientations of a rack comprising two RFID tags can be determined by using a two-dimensional reader antenna matrix.

As shown in FIG. 3A, an exemplary arrangement 300 illustrates reader antennas 318 configured in a two dimensional matrix. The arrangement 300 may be present in a loading/unloading platform for a plurality of sample carriers.

As shown in FIG. 3A, a square rack 310 may be placed in four different orientations as shown by reference numbers 302, 304, 306 and 308. These different orientations may correspond to 0, 90, 180, and 270 degrees of rotation, respectively. The rack 310 shown in FIG. 3A can have a similar configuration as the rack 200 shown in FIG. 2A. The rack 310 in FIG. 3A comprises a first RFID tag 314 and a second RFID tag 316. The first RFID tag 314 is at a center portion of the rack 310, while the second RFID tag 316 is proximate an edge of the rack and is proximate a midpoint of the edge.

Reference number 312 marks a corner with frame of reference for the rack 310. In some embodiments of the invention, reader antennas 318 may be positioned beneath or within an area on which rack 310 is placed. For example, the reader antennas 318 may be positioned beneath loading/unloading platform 108 where the rack 310 may be placed as part of the racks 106 so that the automatic equipment 104 can load or unload sample containers in the rack 310. The loading/unloading platform may take any form, including a horizontal plane in a large drawer or on a countertop. In one embodiment, the reader antennas 318 may be communicatively coupled to a computer (e.g., in the automatic equipment 104) for controlling the orientation and location of the rack 310.

In one embodiment of the invention, the first RFID tag 314 defines the origin of the rack 310 and its geometry. The second RFID tag 316 can be used with the first RFID tag to define the orientation of the rack 310 relative to the two dimensional matrix of the RFID reader antennas 318. In some embodiments, the second RFID tag 316 may comprise a unique value, e.g. in its ID, defining a particular direction within the frame of reference 312 relative to the origin of the rack 310. The first and second RFID tags 314 and 316 in the rack 310 can uniquely align with two antennas in the reader matrix 318 so that the location and the orientation of the rack 310 can be determined. In one embodiment, a computer (e.g., in automatic equipment 104) coupled to the reader antennas 318 may be configured to activate each reader antenna 318. The computer may also be configured to associate the first and second RFID tags with the reader antennas 318 in the reader antenna matrix to the reader antennas' physical locations. Due to the limited reading range of the reader antennas 318, in embodiments of the invention, the accidental reading of tag antennas aligned with adjacent reader antennas is avoided, thus minimizing reader collisions.

In the first exemplary configuration 302, the first RFID tag 314 is aligned with a reader antenna 320 and the second RFID tag 316 is aligned with a reader antenna 322. The exemplary configuration 302 indicates 0° rotation of the rack 310 based on the rack origin from the first RFID tag 314 and a direction from the second RFID tag 316 relative to the matrix of reader antennas 318. The automated equipment 104 may detect that the rack 310 is orientated 0° relative to the frame of reference 312.

In the second exemplary configuration 304, the second RFID tag 316 is aligned with another reader antenna 324. The exemplary configuration 304 indicates a 90° rotation of the rack 310, relative to the orientation of the rack 310 in the configuration 302. The second exemplary configuration is based on the rack origin from the tag 314 and a direction to the tag 316 relative to the matrix of reader antennas 318. The automated equipment 104 may detect that the rack 310 is orientated 90° relative to the orientation of the rack 310 in the first configuration 302 and the frame of reference 312.

In the third exemplary configuration 306, the second RFID tag 316 is aligned with another reader antenna 326. The third exemplary configuration 304 indicates 180° rotation of the rack 310 relative to the orientation of the rack 310 in the first exemplary configuration 302. The third exemplary orientation may be based on a direction from the origin of the rack 210 from the first RFID tag 314 to the second RFID tag 316, relative to the matrix of reader antennas 318. The automated equipment 104 may determine that the rack 310 is orientated 180° relative to the frame of reference 312.

In the fourth exemplary configuration 308, the second RFID tag 316 is aligned with another reader antenna 328. The exemplary configuration 304 shows a 270° rotation of the rack 310 relative to the orientation of the rack 310 in the first exemplary configuration 302. The fourth exemplary configuration is determined using a direction from the rack origin from the first RFID tag 314 to the second RFID tag 316, relative to the matrix of reader antennas 318. The automated equipment 104 may determine that the rack 310 is orientated 270° relative to the frame of reference 312.

FIG. 3A also illustrates a circular rack 330 in four different configurations that are rotated by 90 degrees as in the square rack examples described above. Note that the first and second RFID tags 314 and 316 can be uniquely aligned with two reader antennas, in order to determine the location and orientation of the rack 330. For example, in the exemplary arrangement 302, the second RFID tag 316 is aligned with a reader antenna 332. In the first exemplary configuration 304, the second RFID tag 316 is aligned with a reader antenna 334. In the second exemplary configuration 306, the second RFID tag 316 is aligned with a reader antenna 336. In the exemplary arrangement 308, the second RFID tag 316 is aligned with a reader antenna 338. Thus, the origin of the rack 310 and its orientation relative to the RFID reader antenna matrix is ascertained.

Figure 3B:
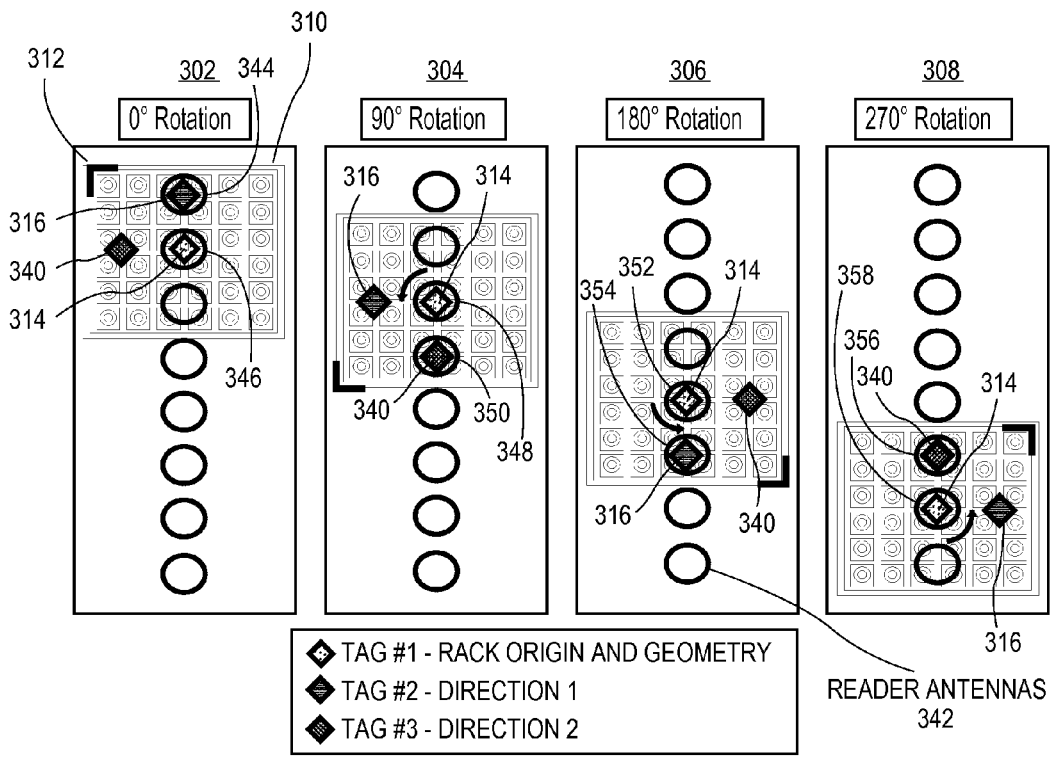
FIG. 3B illustrates different orientations for a rack using a one-dimensional reader antenna matrix, in one embodiment of the invention.

FIG. 3B illustrates different orientations for a rack using a one-dimensional reader antenna matrix according to one embodiment of the invention.

In an exemplary arrangement, as shown in FIG. 3B, reader antennas 342 may be configured in a one dimensional matrix. Reader antennas 342 may be positioned beneath or within an area on which rack 310 is placed. For example, the reader antennas 342 may be positioned beneath or within loading/unloading platform 108 where the rack 310 may be placed as part of the racks 106 so that the automatic equipment 104 can load or unload sample containers in the rack 310. In one embodiment, the reader antennas 342 may be communicatively coupled to a computer (e.g., in the automatic equipment 104) for controlling the orientation and location of the rack 310.

As discussed with reference to FIG. 3A, the first RFID tag 314 defines the origin and geometry of the rack 310 and the second RFID tag 316 defines a first direction relative to the origin. A third RFID tag 340 defines a second direction relative to the origin. The second and third RFID tags 316, 340 can be used to determine and define an orientation of the rack 310 relative to the one dimensional matrix of the RFID reader antennas 342.

At least two of the RFID tags out of the first, second, and third RFID tags 314, 316, 340 in the rack 310 align uniquely with at least two antennas 342 in the reader matrix. For example, in the exemplary first configuration 302, the first RFID tag 314 is aligned with a reader antenna 346 and the second RFID tag 316 is aligned with a reader antenna 344. The third RFID tag 340 is not aligned with any reader antenna in this example. In the exemplary second configuration 304, the RFID tag 314 is aligned with a reader antenna 348 and the RFID tag 340 is aligned with a reader antenna 350. The second RFID tag 316 is not aligned with any reader antenna. In the third exemplary configuration 306, the first RFID tag 314 is aligned with a reader antenna 352 and the second RFID tag 316 is aligned with a reader antenna 354. The third RFID tag 340 is not aligned with any antenna. In the fourth exemplary configuration 308, the first RFID tag 314 is aligned with a reader antenna 358 and the third RFID tag 340 is aligned with a reader antenna 356. The second RFID tag 316 is not aligned with any antenna. In one embodiment, a computer coupled to the reader antennas 342 may activate each reader antenna 342 and associate the RFID tags that are aligned with the reader antennas to the orientation and location of the rack 310. Thus, the origin of the rack 310 and its orientation relative to the RFID reader antenna matrix is ascertained.

Some methods according to embodiments of the invention may including aligning two or more RFID tags of a sample carrier with an RFID reader antenna matrix in such a way so that each of the at least two RFID tags is brought into close proximity to an individual RFID reader antenna. The presence, the position, and the characteristics (e.g., the sample carrier geometry) of the sample carrier can be detected with the RFID antenna matrix.

In some cases, the sample carrier geometric information may be obtained directly from the RFID tag that defines the origin or is obtained from a database comprising a list of sample carrier types, their respective geometry information, and optionally corresponding sample containers or other objects that can be carried by the sample carrier types. By using this information, a sample container or sample containers within a sample carrier can be located in the area. A sample container transport device such as a gripper unit may then be manipulated to handle one or more sample containers within the area.

A display associated with a computer apparatus in electrical communication with the RFID antenna matrix may then display one or more sample carriers and/or sample containers in the area on a graphical user interface.

Some embodiments of the invention can have areas for rack (or other sample carrier) placement (e.g. input or output drawers), where racks can be placed by the user. The areas may be examples of mount devices for mounting racks. The areas may be any area (e.g., input area, output area, or a distribution area) where racks can be placed or exchanged. The areas may comprise a grid, which defines a variety of valid positions for rack placement. This grid may be realized by a mechanical structure, e.g. recesses, pegs, bases, which corresponds to respective mechanical structures of the racks (e.g. rims, holes, etc.). The grid will allow the user to freely choose the position of rack of various sizes as long as all racks are aligned with the grid. The orientation of the racks can be determined automatically via a combination of three tags on each rack (one origin tag (comprising geometric rack information), and two orientation tags, one for each orthogonal axis of rack orientation).

By reading the tags, the system learns what rack is placed on which segments of the rack placement area. By reading the memory of the origin RFID tag in the rack, the system learns e.g. on which positions samples containers may be held by the rack so that a gripper of the system can specifically grip individual samples. The memory of the origin RFID tag may also comprise information related to the kind of samples that fit into the rack, so, e.g., the system can learn from reading the origin tag that a STAT (short turnaround time) tube rack was inserted, and that the tubes in the tube rack should be handled with priority.

These concepts can be described with reference to FIGS. 3C-1, 3C-2, 3C-3, and 3C-4. FIG. 3C-1 shows a rack placement area with a grid 370. FIG. 3C-2 shows a rack placement area with the grid 370 and a one-dimensional array of RFID antennas 374. FIG. 3C-3 shows a square shaped rack (recesses for sample tubes are not shown) 380 with an origin RFID tag 380(a), and a first orientation RFID tag 380(b), and a second orientation RFID tag 380(c).

Figure 4:
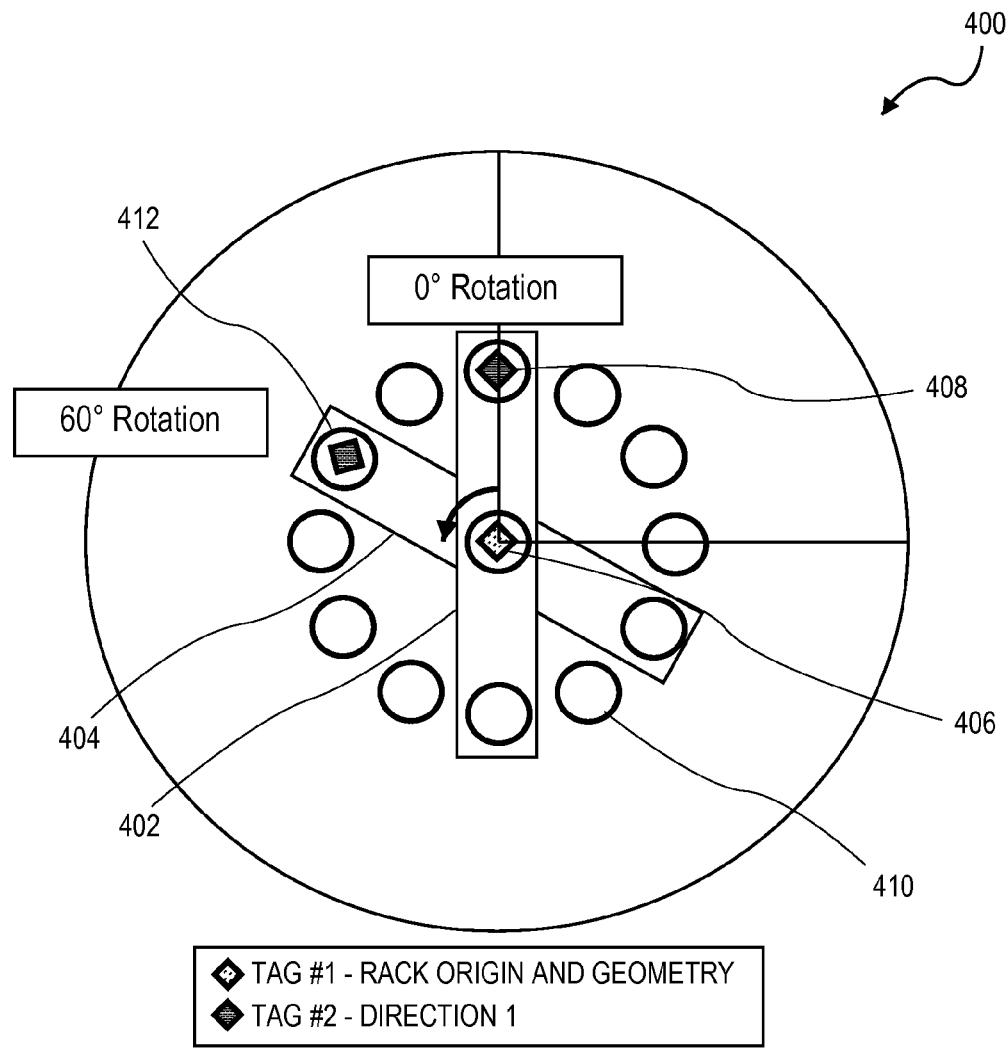

FIG. 3C-4 shows examples of valid rack placements on the grid 370. The rack orientation is automatically detected. For example, rack 380 can have an origin RFID tag 380(a), and a first orientation RFID tag 380(b), and a second orientation RFID tag 380(c). The first orientation RFID tag 380(b) and second orientation RFID tag 380(c) form a right angle with respect to the origin RFID tag 380(a). In this example, the origin RFID tag 380(a) and the second RFID tag 380(c) can be detected by the underlying RFID antenna matrix. The orientation of the rack 380 can be determined, because the origin RFID tag 380(a) is known. The origin RFID tag 380(a) may comprise information regarding the rack geometry, including the position of the first orientation RFID tag 380(b) and second orientation RFID tag 380(c) in relation to the origin RFID tag 380 (a). In another example, the rack 390 can have an origin RFID tag 390(a), a first orientation RFID tag 390(b), and a second orientation tag 390(c). In this example, the origin RFID tag 390(a) and the second orientation RFID tag 390(c) can be detected.

A general workflow that can be used in embodiments of the invention is described below. In embodiments of the invention, a rack placement area can have a defined grid, indicating the valid positions for rack placement. The grid may be defined by e.g. lines or preferably mechanical structures. The grid is preferably orthogonal, thus limiting the options of placement orientation of the racks to 4 (0°, 90°, 180°, 270°). Some racks may be too large in relation to the rack placement area to be placed in all 4 orientations. In such cases, only two placement orientations may be possible. Corresponding to the grid is an array of RFID reader antennas, e.g. one antenna is placed in each field defined by the grid. The array may also be only one-dimensional, e.g., a row of RFID antennas along the longitudinal axis of the rack placement area.

And in some embodiments, a corresponding rack (or other sample carrier) may have exactly one remaining RFID tag in addition to an origin RFID tag. Such a rack may, for example, be used where that rack is placeable in only two possible orientations on the rack placement area due to a width limitation of the rack placement area in relation to the dimensions of the rack. In other embodiments, a corresponding rack (or other sample carrier) may have exactly two remaining RFID tags in addition to an origin RFID tag. Such a rack may, for example, be used where the placement orientation of the rack on the rack placement area is only limited by a grid of valid positions for rack placement on the rack placement area, but, at least for some placement positions, not limited by the boundaries of the rack placement area.

Racks suitable for use on the above rack placement area can have at least two RFID tags that can align with the antenna matrix in the rack placement area, when the rack is interfacing with the grid structures of the rack placement area. The number of tags applied to the rack can depend on the layout of the RFID reader antenna matrix of the rack placement area. If at least two RFID tags are aligned with RFID reader antennas in every possible placement position of the rack, the orientation of the rack can be determined unequivocally.

However, a situation is possible, where the orientation of the rack can also be determined by physical limitations in combination with only one detected RFID tag. So, for example, a square shaped rack, corresponding to the size of 3×3 grid cells of the rack placement area, may comprise 4 different RFID tags, each in the middle of each side of the rack. When the rack placement area is also limited to a width of 3 grid cells and the reader matrix is located as a one-dimensional array of RFID reader antennas along one side of the rack placement area, then in each possible orientation of the rack only one RFID tag is aligned with an RFID reader antenna of the RFID reader antenna matrix. However, in this setup this is sufficient to determine the orientation in which the rack is placed.

In the RFID reading process, RFID antennas are energized. When an RFID tag is aligned to an antenna in the RFID reader antenna matrix, it answers back, providing its ID (and inherently its position as the reader position is known). The system can then request from said RFID tag stored information, e.g. rack type information.

FIG. 4 illustrates a 60° orientation for a rack using a two-dimensional reader antenna matrix, in one embodiment of the invention. Unlike the prior reader antenna matrix embodiments, the reader antenna matrix is in the form of a circle of reader antennas. Further, the rack in this example is a one-dimensional rack with recesses extending only in one direction.

As illustrated in the FIG. 4, a rack 402 having a one-dimensional array of recesses comprises a first RFID tag 406 and a second RFID tag 408. In one embodiment of the invention, the first RFID tag 406 defines the origin of the rack 402 and its geometry. The second RFID tag 408 defines orientation of the rack 402 relative to the two dimensional matrix of RFID reader antennas 410. As shown in FIG. 4, the rack 404 is oriented 60°, counterclockwise, with respect to the rack 402. The rack origin for the rack 404 as marked by the RFID tag 406 and the RFID tag 408 is aligned with a reader antenna 412.

Embodiments of the invention provide benefits over current solutions by utilizing two or more RFID tags and a matrix of RFID reader antennas such that an operator can load racks in numerous locations and orientations and the automation system is able to determine the locations and the orientations of the racks. The number of detectable locations and orientations can depend on the number of RFID tag antennas in the reader matrix, and spacing of the RFID tags in the rack. Thus, the automation equipment can determine correct association of position within the rack for removing and depositing the samples in the rack.

II. Embodiments Using at Least One RFID Tag and a Physical Structure

Other embodiments of the invention do not need to use at least two RFID tags in a sample carrier. In other embodiments of the invention, a universal mount device may be used to control the location and/or orientation of a rack within a plane. An RFID tag in the rack may be used to identify the rack and/or its location.

Referring back to FIG. 1A, the operator 102 of automation equipment 104 may need to accommodate various workflows and/or classifications of sample containers (e.g., sample tubes). For example, the sample containers may need to be classified for further processing such as sorting, capping, decapping, archiving, aliquoting, etc., which may require different workflows. Hence, it may be desirable for the operators to have the flexibility of using multiple sizes of the sample carriers (e.g., racks or trays holding the sample tubes) with the automation equipment 104 without altering any facet of the system. For example, the automation equipment 104 may need to place racks or trays with different sizes onto a drawer (e.g., in an input module). Further, the automation equipment 104 may need to locate racks or trays with different sizes placed on the bottom plane of the drawer so that the system can access the contents of the sample containers stored in sample carriers within the drawer.

Conventional solutions allow a single arrangement of rack types and positions in a drawer. They lack the flexibility of changing the configuration to match work flow or rack sizes. Other solutions make use of a base frame structure that allows for the use of various rack sizes and arrangements. However, each base frame structure may only allow for a single arrangement of rack types and their positions. Consequently, a large number of base frames may be needed to accommodate the many variations of rack types and their various positions on the drawer.

Embodiments of the invention allow the operators flexibility of using multiple rack sizes and arranging them in different ways to accommodate various workflows. In one embodiment, a method is provided that allows for the arrangement of multiple rack types on a drawer (e.g., in an input module of an automation system) in various positions using a universal mount device. The universal mount device may be present in the drawer or capable of being removed from the drawer or the input module of an automation system in embodiments of the invention. In addition, information relating to the racks/trays, their locations and orientations in the drawer are transmitted to the system which can use this information to move samples or sample containers to and from the sample carriers (e.g., racks, trays, etc.).

One embodiment of the invention is directed to a universal mount device comprising a mount body comprising a plurality of patterned features. The plurality of patterned features are capable of positioning sample carriers of different sizes and/or capable of positioning sample carriers at different locations on the mount body. In some embodiments, the locations may be predefined. An RFID reader antenna matrix is coupled to the mount body. The RFID reader antenna matrix may be coupled to the mount body in any suitable manner. For example, in embodiments of the invention, the RFID reader antenna matrix may be embedded within the mount body, in recesses in the mount body, or attached to an outer surface (e.g., top or side surfaces) of the mount body. The RFID reader antenna matrix comprises a plurality of RFID reader antennas. In embodiments of the invention, patterned features associated with the mount body ensure that an RFID tag associated with the sample carrier (e.g., a rack) aligns with a defined reader antenna (of the matrix) in the mount body, when the sample carrier is placed at a defined (by patterned feature) position on the mount body. The RFID tag can comprise information regarding the dimensions of the sample carrier in some embodiments of the invention.

FIG. 5A illustrates a top plan view of a universal mount device according to one embodiment of the invention.

In one embodiment, an exemplary apparatus 500 includes a universal mount device 502 and a rack 504 that may be mounted on the universal mount device 502 in multiple positions. In one embodiment, the universal mount device 502 may include a mount body 520 and an RFID reader antenna matrix 514 comprising a plurality of RFID reader antennas 516 coupled to the mount body 520. The mount body 520 may be in the form of a planar structure, and the RFID reader antennas 516 may be embedded within the mount body 520 or attached to its upper side or underside. The mount body 520 may be made of any suitable material including any suitable polymeric material. The mount body 520 may have any suitable shape that allows arranging of different types/sizes of racks or trays that can be accessed by the automation equipment 102. For example, the mount body 520 may have a circular, square, or a rectangular surface area in some embodiments of the invention.

In FIG. 5A, the universal mount device 502 comprises eight patterned features 518. Each patterned feature 518 may include one or more mount locating features 522 (e.g., in the form of walls of a rectangle) and a mount orientation feature 524, e.g. extending from one of the walls. The patterned features 518 may be raised or recessed, relative to another major surface of the mount body 520, by any suitable distance.

FIG. 5B illustrates a perspective view of the rack 504 mounted on the universal mount device 502, in one embodiment of the invention. It will be understood that the rack 504 can be mounted on any of the eight patterned features 518 of the universal mount device 502. In some embodiments, at least one valid position of the rack 504 on the universal mount device 502 can be defined based on the patterned features of the universal mount device 502.

FIG. 5C illustrates the rack 504 comprising a carrier location feature and a carrier orientation feature, in one embodiment of the invention.

As illustrated in FIG. 5C, the rack 504 may comprise a carrier body 512, an RFID tag 506 coupled to the carrier body 512, a carrier locating feature 508 and a carrier orientation feature 510 associated with the carrier body 512. The rack 504 is capable of being positioned and oriented by interfacing one or more of the patterned features of the universal mount device 502 with the carrier locating feature 508 and the carrier orientation feature 510 associated with the carrier body 512. The rack 504 may hold microtiter plates or as little as one sample. As shown, the RFID tag 506 may be placed within a structure that protrudes downward from the top major surface of the rack 504. This allows the RFID tag 506 to be as close as possible to the reader antennas in the reader antenna matrix.

In FIG. 5A, the RFID reader antenna matrix 514 is configured as a one dimensional matrix of equally spaced RFID reader antennas 516, however, any suitable configuration of the RFID reader antennas is possible (e.g., two dimensional, circular, etc.). Further, although FIG. 5A shows equally spaced RFID reader antennas, in other embodiments, the RFID reader antennas may be unequally spaced. In this example, each reader antenna 516 is disposed either inside a mount locating features or between adjacent pairs of mount locating features 522. As discussed previously, each of the RFID reader antennas 516 may be configured as a radio frequency transmitter and receiver that may be controlled by a computer or a processing unit. The RFID reader antenna matrix 514 may be configured to extract information from the RFID tags that may be affixed to the rack bodies. Such information is either directly extracted from the RFID tag's memory or from a higher level software database according to the identified type or ID information of the RFID tag.

In one embodiment of the invention, the universal mount device 502 is configured to support the mounting of sample carriers such as racks or trays of different sizes/types. Additionally, the universal mount device 502 provides for one or more patterned features 518 on which racks and trays that are compatible with this feature can be located, for example, by using the mount locating feature 522 and the mount orientation feature 524. In an embodiment, a tray may be configured as an adapter that permits racks or other items that are not compatible with the patterned feature of the universal mount device 502 to be located on the universal mount device 502. In another embodiment, the universal mount device 502 may be implemented as a permanent feature on the drawer. In another embodiment, the universal mount device 502 is similar to a base frame that is removable from the drawer to accommodate various rack sizes and types.

In one embodiment, the rack 504 or a tray holding the rack 504 (not shown) is designed to be cooperatively structured with the patterned feature 518 of the universal mount device 502. The carrier body 512 may have any suitable shape including a circular, square or rectangular vertical or horizontal cross section to accomplish this. The carrier body 512 may also have any suitable number of slots or recesses for holding sample containers, in any suitable arrangement. In some embodiments, the slots may be arranged as an array, with equal or unequal numbers of rows and columns.

In one embodiment, the RFID tag 506 may be affixed to the rack 504 e.g. in a central position such that it aligns with an RFID reader antenna on the universal mount device 502 when the rack is placed in such a manner on the universal mount, that the carrier locating features of the rack and the mount locating feature of the universal mount are interfacing with each other. When an RFID tag 506 is brought into close proximity of the field of a scanning RFID reader antenna 516, it is activated by the field of the scanning RFID antenna and its ID may be read by the RFID reader antenna. Via software running on a processor, multiple or specific RFID tags can be triggered by the RFID reader antenna to transmit the information stored on the microchip to be picked up by the scanning RFID antenna. The information associated with the RFID tags 506 may include a unique identifier of the rack or tray, information regarding the rack 504 or a tray holding the rack 504, for example, a color of the rack or tray, a type of the rack or tray, geometric information related to the rack or tray and information regarding the location of one or more positions on the rack or tray where sample containers or samples may be held by the rack or tray. Such rack specific information may e.g. further comprise information related to sample tubes that will fit into the respective rack. In one embodiment, the central position of the RFID tag 506 aligns with an RFID reader that may be part of the RFID reader antenna matrix 514. The RFID readers in the RFID reader antenna matrix 514 may have limited range that prevents them from reading any RFID tag other than the one directly over the antenna. As each antenna in the RFID reader antenna matrix 514 is energized, some of the RFID reader antennas 516 may read the RFID tag associated with a rack/tray, while others may not. Since the patterned feature of the universal mount device 502 is defined relative to the positions of the RFID reader antennas 516, if an RFID reader antenna 516 reads an RFID tag, the rack to which the tag is attached can be associated to a feature position on the universal mount device 502.

With respect to the universal mount device 502 in FIG. 5A, a number of wires and other electrical components may connect the RFID reader antenna matrix 514 to a computer apparatus (e.g., the computer apparatus 104B in FIG. 1B). These wires are not shown for simplicity of illustration, and one of ordinary skill in the art would know how to provide for any suitable electrical communication between the RFID reader antenna matrix 514 and a computer apparatus.

The rack 504 may comprise one or more carrier locating features 508, and one or more carrier orientation features 510. The carrier locating features 508 and the carrier orientation features 510 may be integrally formed with the carrier body 512 as illustrated in FIG. 5C, or they may be separate structures attached to the carrier body 512. In this example, there are two locating features in the rack 504, each locating feature embodied by parallel walls. The parallel walls may interface (e.g., contact) with the parallel sides of a single patterned feature 518 or multiple patterned features 518 utilizing the mount locating feature 522 and the mount orientation feature 524 so that the rack 504 is accurately positioned on the universal mount device 502. The carrier orientation feature 510 in this example is embodied by a recess in one of the walls of the rack 504. In other embodiments, the carrier orientation features may in the form of specific structures such as protrusions. The one or more carrier locating features 508 and the carrier orientation feature 510 allow for the accurate location and orientation with respect to the one or more patterned features of the universal mount device 502.

The carrier locating feature 508 and the carrier orientation feature 510 may have other suitable characteristics. For example, in one embodiment, the carrier locating feature 508 may be related to the geometrical dimensions (e.g., length and width) of the rack 504. In one embodiment, the carrier orientation feature 510 may comprise a slot or an opening that may be used as a reference for placing or locating the rack 504 on the universal mount device 502 at a specific position. In one embodiment, the geometric location of the universal mount device 502 and its patterned feature are defined relative to the drawer, which help determine the locations of the racks/trays relative to the drawer. The geometric information regarding the rack 504 extracted from the RFID tag 506 permits the identification of the geometric locations of the accessible sites of the rack 504. The information may be conveyed to the automation equipment 104 that may use this information to move the sample containers to and from the rack 504.

Figure 6:
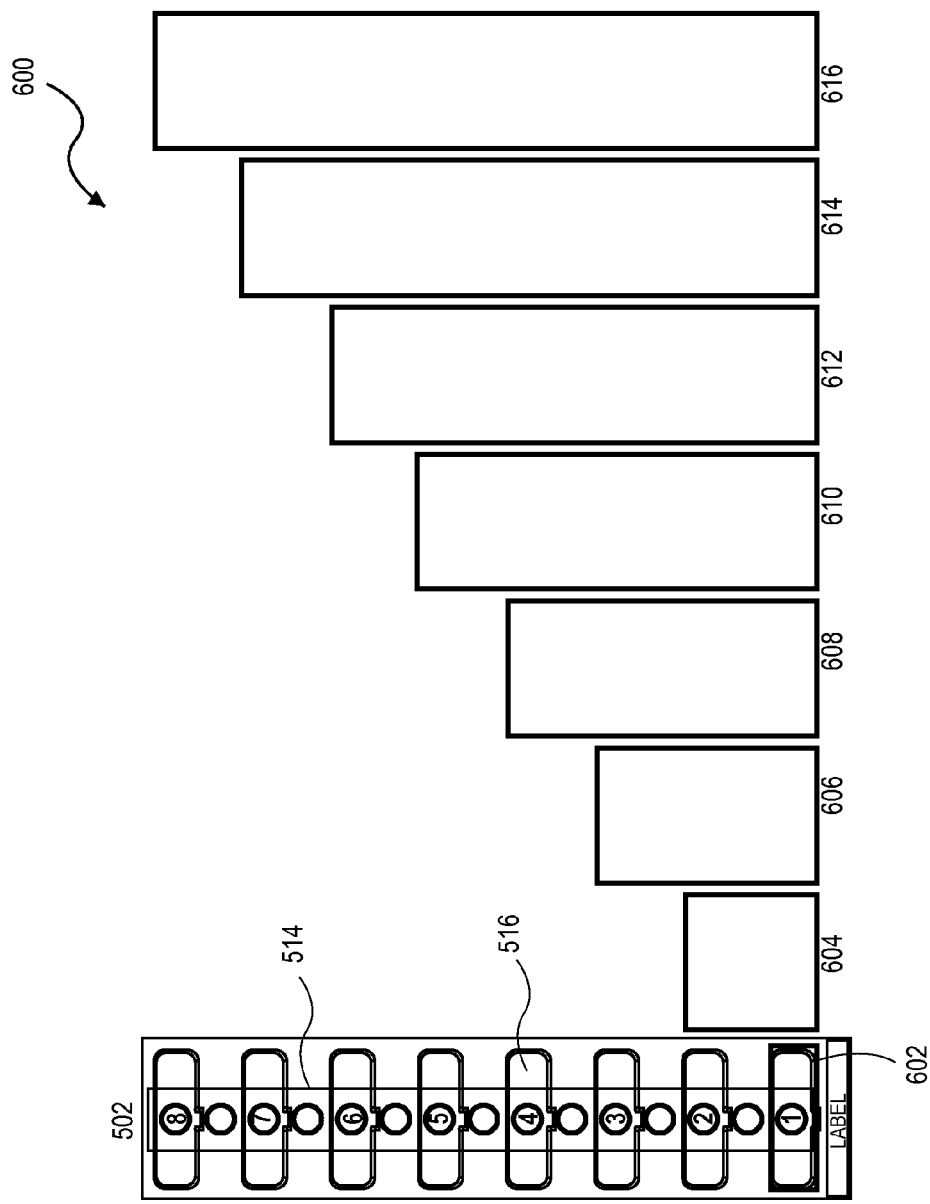
FIG. 6 illustrates exemplary rack sizes compatible with the universal mount device, in embodiments of the invention.

FIG. 6 illustrates exemplary rack sizes compatible with the universal mount device, in accordance with embodiments of the invention.

As illustrated, increasing rack sizes 602, 604, 606, 608, 610, 612, 614 and 616 are compatible with the universal mount device 502. In embodiments of the invention, a rack/tray size is compatible if it incorporates the patterned feature of the universal mount device 502. For example, the rack 604 may be similar to the rack 504 with an RFID tag similar to the RFID tag 506 that can be read by RFID reader antennas of the RFID reader antenna matrix 514. In some embodiments, one or more of the rack sizes 602, 604, 606, 608, 610, 612, 614 and 616 denote rack sizes that are compatible with the universal mount device 502. Racks or other items that do not possess the patterned feature of the universal mount device 502 cannot be located or placed on the universal mount device 502. In some embodiments, each of the racks or trays may have an RFID tag affixed in a central position that may be detected by one of the RFID reader antennas of the RFID reader antenna matrix 514. For example, if a rack as the size designated by reference number 604, the rack may have a single RFID tag at a central portion of the rack. When the rack is placed over the mount locating features 516 that are labeled "1" and "2", an RF antenna between these mount locating features 516 can activate and obtain information from the single RFID tag. That single RFID tag may store information (e.g., in a memory) regarding the dimensions of the rack. In this case, a computer apparatus coupled to the reader antenna will be able to determine that the rack is currently located over the mount locating features that are labeled "1" and "2".

Figure 7A:
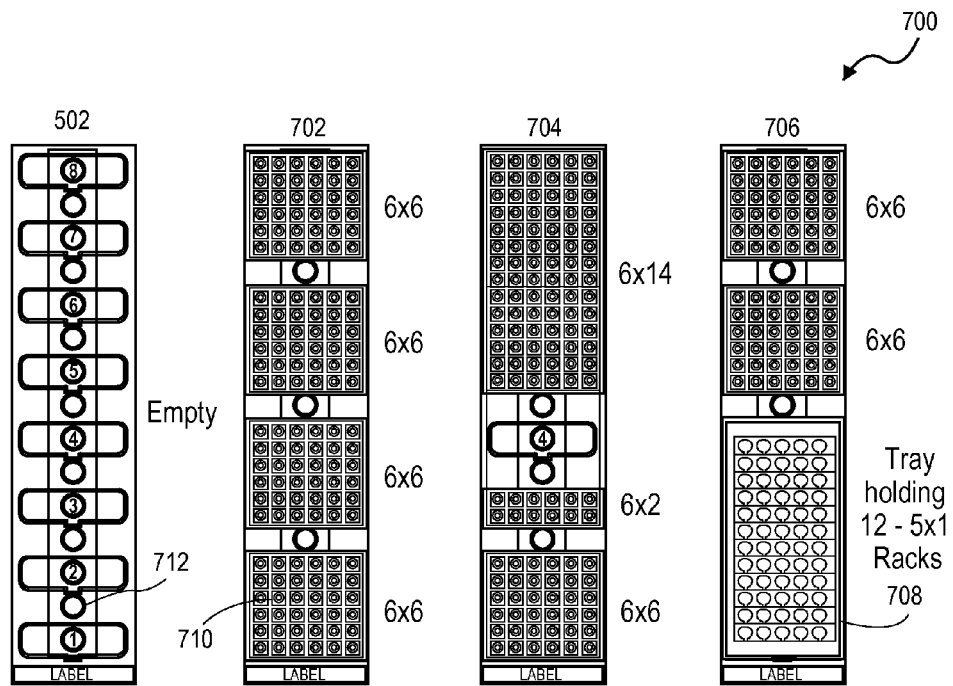
FIGS. 7A-7B illustrate exemplary rack/tray arrangements on the universal mount device, in embodiments of the invention.
Figure 7B:
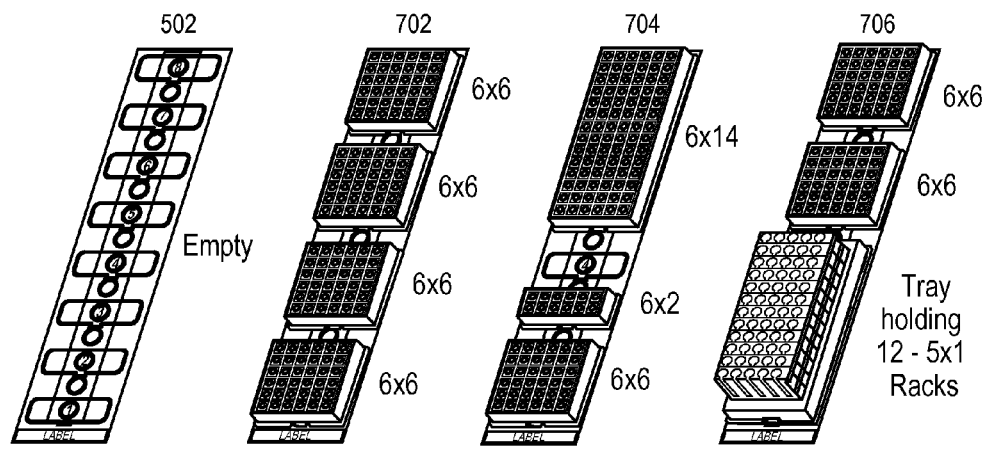

FIGS. 7A-7B illustrate exemplary rack/tray arrangements on the universal mount, in embodiments of the invention.

As illustrated in FIG. 7A (which shows top plan views), in a first exemplary configuration 702, four 6×6 racks may be arranged on the universal mount device 502. In a second exemplary configuration 704, one 6×14 rack, one 6×2 rack and one 6×6 rack may be arranged on the universal mount device 502. In third exemplary configuration 706, two 6×6 racks and one tray 708 holding twelve 5×1 racks may be arranged on the universal mount device 502.

In the first exemplary configuration, the rack 710 may have an RFID tag in a central location in the rack. The RFID tag of the rack 710 may align with an RFID reader antenna 712 so that the geometric information regarding the rack 710 is extracted and associated to a feature position on the universal mount device 502.

In the third exemplary configuration 706, the sample carrier 708 holds twelve 5×1 racks. Each of the 5×1 racks may not possess the patterned feature of the universal mount device 502. However, an RFID tag (not shown) affixed to the sample carrier 708 may be in a central position such that it aligns with an RFID reader antenna on the universal mount device 502 and extracts relevant information for identifying the racks placed in the sample carrier 708 to thereby identify the sample positions in the racks.

FIG. 7B illustrates a side, perspective view of the exemplary universal mount device 502 and configurations 702, 704 and 706 using the universal mount device 502 according to embodiments of the invention.

As illustrated in FIGS. 7A-7B, embodiments of the invention allow arranging different sizes/types of racks or trays in multiple positions using a universal mount device. In embodiments of the invention, a sample carrier is capable of being positioned by interfacing one or more of the patterned features of the universal mount device with the locating feature and the orientation feature of the sample carrier. Thus, embodiments of the invention provide flexibility to the operators of the automation systems by allowing the access of multiple rack/tray sizes to accommodate various workflows or classification of samples.

Further, referring back to FIG. 5A, the mount orientation feature 524 provides a physical control for detecting the orientation of the rack 504 and the RFID tag 506 allows detecting the location of the rack 504 on the universal mount device 502. In some embodiments, the mount orientation feature 524 of the universal mount device 502 may be combined with the multiple RFID tags of the rack 200 to determine the location and orientation of the racks on the universal mount device 502. By utilizing the mount orientation feature for physical control may allow for fewer RFID reader antennas, since the position of the rack may be somewhat confined. This can decrease the complexity and cost of the system, relative to other configurations.

The various participants and elements described herein with reference to the figures may operate one or more computer apparatuses to facilitate the functions described herein. Any of the elements in the above description, including any servers, processors, or databases, may use any suitable number of subsystems to facilitate the functions described herein, such as, e.g., functions for operating and/or controlling the functional units and modules of the laboratory automation system, transportation systems, the scheduler, the central controller, local controllers, etc.

Figure 8:
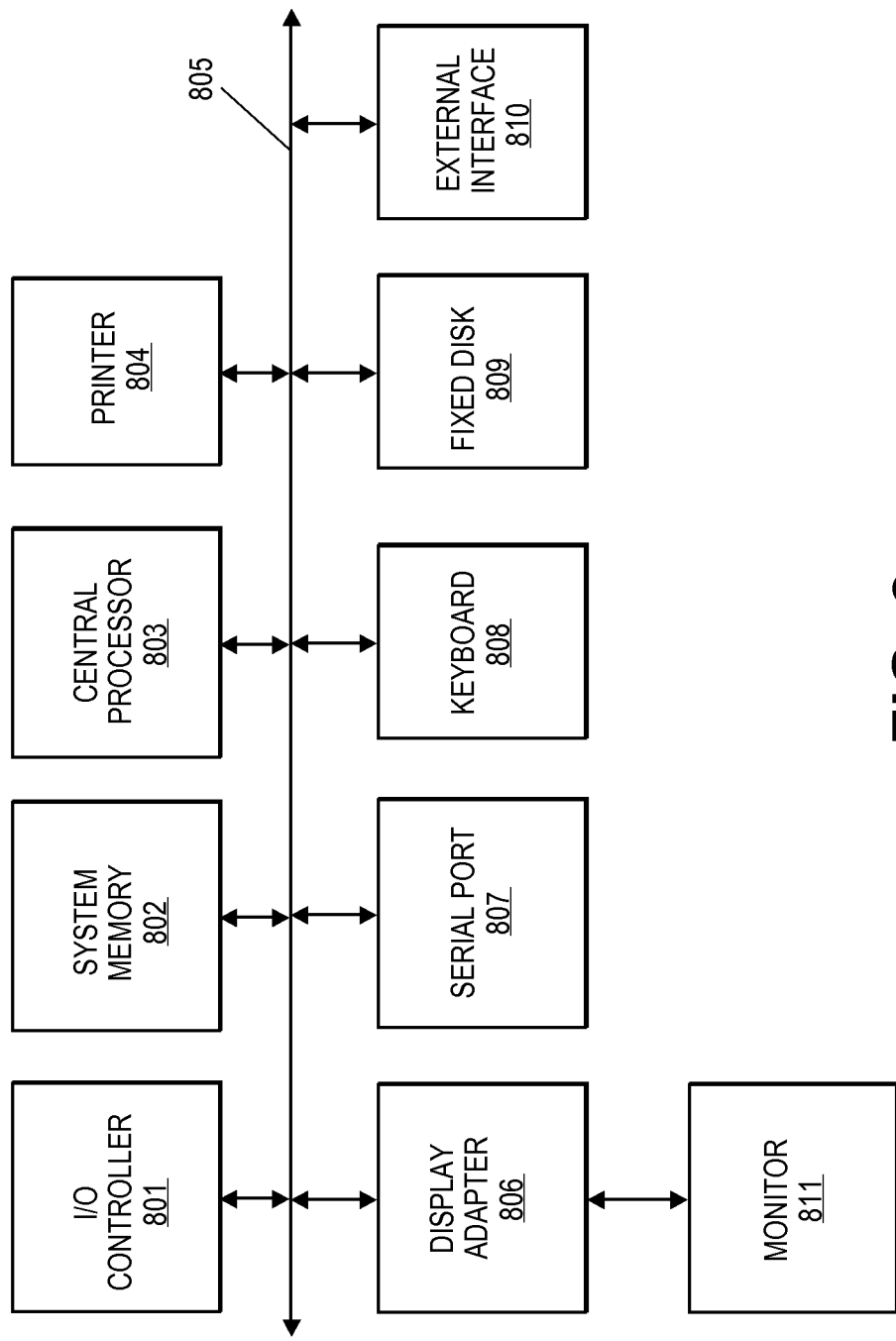
FIG. 8 illustrates a block diagram of an exemplary computer apparatus.

Examples of such subsystems or components are shown in FIG. 8. The subsystems shown in FIG. 8 are interconnected via a system bus 805. Additional subsystems such as a printer 804, keyboard 808, fixed disk 809 (or other memory comprising computer readable media), monitor 811, which is coupled to display adapter 806, and others are shown. Peripherals and input/output (I/O) devices, which couple to I/O controller 801 (which can be a processor or other suitable controller), can be connected to the computer system by any number of means known in the art, such as serial port 807. For example, serial port 807 or external interface 810 can be used to connect the computer apparatus to a wide area network such as the Internet, a mouse input device, or a scanner. The interconnection via system bus allows the central processor 803 to communicate with each subsystem and to control the execution of instructions from system memory 802 or the fixed disk 809, as well as the exchange of information between subsystems. The system memory 802 and/or the fixed disk 809 may embody a computer readable medium.

Embodiments of the technology are not limited to the above-described embodiments. Specific details regarding some of the above-described aspects are provided above. The specific details of the specific aspects may be combined in any suitable manner without departing from the spirit and scope of embodiments of the technology. For example, back end processing, data analysis, data collection, and other processes may all be combined in some embodiments of the technology. However, other embodiments of the technology may be directed to specific embodiments relating to each individual aspect, or specific combinations of these individual aspects.

It should be understood that the present technology as described above can be implemented in the form of control logic using computer software (stored in a tangible physical medium) in a modular or integrated manner. Furthermore, the present technology may be implemented in the form and/or combination of any image processing. Based on the disclosure and teachings provided herein, a person of ordinary skill in the art will know and appreciate other ways and/or methods to implement the present technology using hardware and a combination of hardware and software.

Any of the software components or functions described in this application, may be implemented as software code to be executed by a processor using any suitable computer language such as, for example, Java, C++ or Perl using, for example, conventional or object-oriented techniques. The software code may be stored as a series of instructions, or commands on a computer readable medium, such as a random access memory (RAM), a read only memory (ROM), a magnetic medium such as a hard-drive or a floppy disk, or an optical medium such as a CD-ROM. Any such computer readable medium may reside on or within a single computational apparatus, and may be present on or within different computational apparatuses within a system or network.

The above description is illustrative and is not restrictive. Many variations of the technology will become apparent to those skilled in the art upon review of the disclosure. The scope of the technology should, therefore, be determined not with reference to the above description, but instead should be determined with reference to the pending claims along with their full scope or equivalents.

One or more features from any embodiment may be combined with one or more features of any other embodiment without departing from the scope of the technology.

A recitation of "a", "an" or "the" is intended to mean "one or more" unless specifically indicated to the contrary.

All patents, patent applications, publications, and descriptions mentioned above are herein incorporated by reference in their entirety for all purposes. None is admitted to be prior art.

What is claimed is:

1. A system comprising:
   a mount device comprising a mount body comprising a plurality of patterned features having the same size and shape and an RFID reader antenna matrix physically coupled to the mount body, the RFID reader antenna matrix comprising a plurality of RFID reader antennas; and
   a sample carrier comprising a carrier body comprising at least one recess for holding sample containers or samples, a carrier locating feature associated with the carrier body, a carrier orientation feature associated with the carrier body, and an RFID tag physically coupled to the carrier body, wherein the sample carrier is capable of being positioned on the mount body by interfacing one or more of the patterned features with the carrier locating feature and the carrier orientation feature, wherein the plurality of patterned features comprise a mount orientation feature configured to engage with the carrier orientation feature of the sample carrier to engage distinct carrier orientation features of the sample carriers to fix a rotational orientation of the sample carrier with respect to the mount orientation feature in a distinct desired orientation.

2. The system of claim 1, wherein the RFID tag is affixed to the carrier body of the sample carrier in a central position that aligns with at least one of the plurality of the RFID reader antennas, when the sample carrier is positioned on the mount body.

3. The system of claim 1, further comprising an input module wherein the mount device is present in the input module.

4. The system of claim 1, wherein the input module is part of a laboratory automation system.

5. The system of claim 3, wherein the mount device is capable of being removed from the input module.

6. The system of claim 1, wherein at least one valid position of the sample carrier on the mount device can be defined based on the patterned features of the mount device.

7. A method of using the system according to claim 1, the method comprising:
   placing the sample carrier on the mount device, such that the one or more patterned features interface with the carrier locating feature and the carrier orientation feature.

8. The method of claim 7, further comprising:
   activating at least one RFID tag of the sample carrier via the reader antenna matrix;
   reading-out RFID tag information from at least one RFID tag; and
   determining the position of the at least one recess for holding sample containers or samples by using the read-out information obtained by reading the at least one RFID tag.

* * * * *